United States Patent [19]
Chirife

[11] Patent Number: 5,179,949
[45] Date of Patent: Jan. 19, 1993

[54] CARDIAC PACEMAKER WITH AUTOMATIC A-V PROGRAMMING FOR OPTIMIZATION OF LEFT HEART A-V INTERVAL

[76] Inventor: Raul Chirife, Pirovano 137, 1650 Martinez, Buenos Aires, Argentina

[21] Appl. No.: 624,047

[22] Filed: Dec. 7, 1990

[51] Int. Cl.$^5$ ............................................. A61N 1/368
[52] U.S. Cl. ................................................ 128/419 PG
[58] Field of Search ................................... 128/419 PG

[56] References Cited

U.S. PATENT DOCUMENTS

| | | | |
|---|---|---|---|
| 4,412,541 | 11/1983 | Schaldach et al. | 128/419 PG |
| 4,421,116 | 12/1983 | Markowitz | 128/419 PG |
| 4,452,248 | 6/1984 | Keller, Jr. | 128/419 PG |
| 4,485,818 | 12/1984 | Leckrone et al. | 128/419 PG |
| 4,539,991 | 9/1985 | Boute et al. | 128/419 PG |
| 4,554,921 | 11/1985 | Boute et al. | 128/419 PG |
| 4,624,260 | 11/1986 | Baker, Jr. et al. | 128/419 PG |
| 4,712,555 | 12/1987 | Thornander et al. | 128/419 PG |
| 4,799,486 | 1/1989 | DuFault | 128/419 PG |
| 4,802,483 | 2/1989 | Lindgren | 128/419 PG |
| 4,856,524 | 8/1989 | Baker, Jr. | 128/419 PG |
| 4,890,617 | 1/1990 | Markowitz et al. | 128/419 PG |
| 4,920,965 | 5/1990 | Funke et al. | 128/419 PG |
| 4,932,406 | 6/1990 | Berkovits | 128/419 PG |
| 4,940,052 | 7/1990 | Mann et al. | 128/419 PG |
| 4,940,053 | 7/1990 | Mann et al. | 128/419 PG |
| 4,945,909 | 8/1990 | Fearnot et al. | 128/419 PG |

*Primary Examiner*—William E. Kamm
*Assistant Examiner*—Kennedy J. Schaetzle
*Attorney, Agent, or Firm*—Haugen and Nikolai

[57] ABSTRACT

A dual-chamber AV sequential pacemaker with the capability of automatically adjusting right heart AV interval to optimize left heart AV interval by compensating for pacing-induced inter-atrial and inter-ventricular conduction delays. Depending on the pacing and sensing action, as determined by the patient's native rate, the predetermined threshold rate and intrinsic AV interval, the pacemaker selects the AV interval. Right heart AV interval is adjusted to compensate for the heart's inter-atrial and inter-ventricular delays. Threshold values are previously estimated, using mean values measured using non-invasive techniques. The pacemaker has a dual phase operating mechanism consisting of an analysis phase followed by a pacing phase. The P wave rate is sensed and compared to a predetermined base rate. If the sensed P wave rate is above the baseline, atrial depolarizations will be sensed by the pacemaker and small number (default=4) of consecutive native AV intervals will be averaged. If this average is less than a predetermined threshold value, the system will continue in the demand mode, sensing P and R waves. If the average is greater than said value, then the ventricle is paced for n number of times the analysis phase (default=100 cycles), each followed by a short AV delay (Default=50 ms) that is intended to compensate for the delay introduced in the onset of left ventricular depolarization after pacing the right ventricular apex. When P wave rate is below the predetermined rate, atrial pacing will occur.

9 Claims, 4 Drawing Sheets

CARDIAC PACEMAKER WITH AUTOMATIC A-V PROGRAMMING FOR OPTIMIZATION OF LEFT HEART A-V INTERVAL

BACKGROUND OF THE INVENTION

I. Field of the invention

This invention relates generally to the design of cardiac pacemakers, and more particularly to a dual-chamber atrioventricular (AV) sequential pacemaker having the capability of automatically adjusting the right heart AV interval in order to optimize the left heart AV interval. It accomplishes this by compensating for pacing-induced inter-atrial and inter-ventricular conduction delays known to produce impairment of ventricular function in prior art pacers.

II. Discussion of the Prior Art

The technique of cardiac pacing provides electrical stimulation of the myocardium when normal, intrinsic stimuli are absent or too slow. Beginning at the site of the stimulating electrode, an electrical wave, or depolarization, spreads through existing pathways in the myocardium as if the stimulus were natural. However, typical pacing electrodes are rarely placed near the site of origination of normal sinus beats. They are usually placed on the wall of the right atrial appendage or near the apex of the right ventricle. By virtue of this placement, an artificially stimulated depolarization must travel different distances across the heart, thus utilizing pathways that an intrinsic sinus beat would not.

A normal contraction cycle in the heart, shown in FIG. 1, begins at the sinoatrial node (302) in the wall of the right atrium (304) near the superior vena cava (306). Specialized nervous tissue located there has enhanced capacity to produce an action potential and thus is capable of overriding the ability of all cardiac muscle cells to initiate a contraction. Due to the enhanced ability of these cells to perform cyclical depolarization and repolarization, this locus is known as the heart's natural pacemaker. The depolarization spreads from this site at about 1 meter per second into both the right (308) and left (310) atria then atrial appendages (312, 314) causing atrial contraction. Thus, in normal subjects, right and left atrial contraction occurs within a period of 15 to 20 msec of each other.

The wave eventually reaches the atrioventricular (AV) junction (316), which is specialized for slow conduction. This is the only normal electrical connection between the atria and the ventricles and it assures that atrial contraction is completed before the ventricles are stimulated. As the stimulus is passed on to the ventricles, it reaches the specialized fibers of the bundle of His (318) and the Purkinje fibers (paths F-G-H and F-J-K). These fibers conduct at a much higher rate than the atrial muscle, about 5 meters per second. These specialized fibers form a network over the ventricles and thus distribute to clusters of true cardiac muscle (324, 332) the stimulus to depolarize. This process is not exactly simultaneous due to the fact that the stimulus tends to descend the right bundle branch (320-322) slightly more slowly (0.01 sec) than the left bundle branch (330-332). Therefore, the left and right surfaces of the interventricular septum (326) are stimulated differently so that the depolarization moves from left to right. However, this difference is not very apparent when considering the entire ventricular conduction period, because once the wave reaches the ventricular free walls (340, 350), it travels its perpendicular path more quickly on the right (350). This is due to the significantly smaller right muscle mass of the thinner right free wall and thus compensates somewhat for the prior delay. In this manner, normal ventricular depolarization is almost simultaneous and is completed in less than 0.1 second. Thus, the atrial to ventricular contraction sequence occurs almost simultaneously for left and right sides of the heart.

A typical lead configuration as known in the art for pacing both atrium and ventricle is shown in FIG. 2. A catheter 12 is fit into the right atrium and another catheter 14 in the tip of the right ventricle. Both may have one or two electrodes, one of them placed at each tip. Electrical stimuli may be delivered at either locus and will be transferred by cardiac tissue in the normal manner, as described more fully hereinafter.

A summary of normal conduction pathways is provided by the heart shown in FIG. 3a. A normal depolarization is initiated at the sinoatrial node (A). It spreads to the right atrial appendage (B), the inter-atrial septum (C), the left atrium and appendage (D) and the atrioventricular node (E). It crosses into the ventricles and reaches the bundle of His (F). It then splits and runs parallel the two sides of the septum (F to G, G to H; F to J, J to K) following the right bundle branch (F to G to H) and the left bundle branch (F to J to K). It then spreads out to the Purkinje system and the individual cardiac muscle fibers of the right (I) and left (L) ventricles.

Cardiac pacing interferes with this normal cycle because typical paced beats are not initiated at the sinoatrial node (A) as native beats are. A typical atrial beat, therefore, is required to follow an abnormal depolarization pathway in order to reach the ventricles.

An example of such an abnormal depolarization pathway is that which results when a pacing electrode is placed on the right atrial appendage, as shown in FIG. 3b. The stimulus travels from the point of electrode placement A' towards the base of the appendage. As previously described, this conduction occurs by passing the stimulus from muscle cell to muscle cell at only about 1 meter per second in the healthy heart and possibly slower in the diseased heart. This results in a first depolarization and contraction cycle in the right atrium (A' to B', A' to C', A' to E) followed by a second depolarization and contraction cycle in the left atrium (C' to D, E to D). The delay between these two contractions (right and left atrium) has been found to be in the range of 70 to 200 msec.

Another example of an abnormal depolarization pathway is that which occurs during ventricular pacing, as shown in FIG. 3c. A similar delay as in atrial pacing has been observed when the right ventricle is paced. The apex of the right ventricle is stimulated (A") and the depolarization flows along the pathway G-H-I. It also flows retrograde through the bundle branches (A" to B") of the right Purkinje system up to the bundle of His (B") then to the left ventricular Purkinje system (B" to J to K). This results in a delay in depolarization and contraction between the two cavities of 60 to 100 msec. During this process, the much slower ability of cardiac muscle fibers to stimulate one another plays an insignificant role in passing the contraction stimulus through the interventricular septum and from right free wall to left free wall and from the point of stimulation to the left ventricle (A" to J).

This has important implications in treating pathological conditions, since every patient has an optimal AV delay. If the AV delay is either too short or too long, there will be a reduction of ventricular filling and thus a reduction in cardiac output, defined as the quantity of blood moved through the heart per unit of time. The atrial contribution to cardiac output (CO) is well known and has been one of the objectives of the development of dual-chamber, AV sequential pacemakers. However, it has become increasingly apparent that programming a pacemaker to be timed to preserve an AV interval that is within a "physiological" range may be misleading when based upon delivery of pacing pulses to the right atrium and/or ventricle, due to both the aforementioned delays in contraction and the known difficulty in assessing exact timing of left atrial and left ventricular depolarization from a standard surface ECG.

Furthermore, some pathological conditions are intermittent. A well-designed pacemaker should be able to detect then react as intermittent conduction problems spontaneously begin and end. An example of such a condition is intermittent heart block. One way to monitor these conditions is by the standard electrocardiogram depolarization waveform.

Cardiac pacemakers are designed to detect the movement of the depolarization as it spreads across the heart, utilizing the standard electrocardiography PQRST waveform. In certain pathological conditions such as heart block, there may be an excessive lengthening of AV interval causing various degrees of alteration in ventricular function, depending on the timing of the P waves in relation to the QRS complex. If there is an AV dissociation, those beats with properly timed P waves are known to be stronger than those without. Restoration of AV synchrony by artificial pacing in these patients usually improves cardiac function. It must be remembered, however, that true AV synchrony is only attained when the pacemaker used is programmed to account for the differences in conduction times inherent in the process of pacing.

When pacing the atrium and sensing the ventricle, it is possible to account for these differences by calculating the left heart AV interval (LAV) on the bases Of the measured total AV interval (AV) and inter-atrial conduction delay. Using the formula LAV=AV−IACT, it is possible to determine whether the stimulated beats are being conducted within an appropriate range.

Two examples are illustrative:

If the patient suffers from sinus bradycardia and the right atrium is paced with a lead in the right atrial appendage, the patient's own PR interval (i.e., typically 150 ms) will be apparently preserved, as seen on the surface ECG. Since the impulse is originated in the right atrial appendage, it takes some time to reach the left atrium (e.g. 100 ms), so the actual left heart AV interval (LAV) will be considerably shorter (50 ms) and outside the physiologic range.

Likewise, if the patient suffers from third degree AV block and AV sequential pacing is used, pacing the right ventricle 150 ms after a sensed P wave will lengthen left heart AV interval by the duration of inter-ventricular conduction time. Thus, actual left heart AV during atrial sensing-ventrical pacing is the result of adding the measured AV plus the interventricular conduction time.

It is apparent from above observations, that programming a pacemaker to preserve a "physiological" AV interval based on measurements of right-sided events may be misleading, since the left atrial and left ventricular depolarization are difficult to assess from a standard surface ECG. To more appropriately adjust the timing, it is important to know the factors that influence these intervals.

Research was done to separately measure right and left heart AV intervals during different pacing modalities and to assess left ventricular systolic function by systolic time intervals. Inter-atrial conduction time (IACT) was measured from the right atrial pacing spike to the onset of left atrial depolarization, as detected by an esophageal electrode.

Inter-ventricular conduction time is the additional delay caused by right ventricular pacing on the onset of left ventricular activation-contraction. This was assessed by measuring the duration of left heart pre-ejection period both during RV pacing and during spontaneous depolarization. The difference between these modes of initiating a contraction is thus an approximation of the inter-ventricular conduction time.

The above research has shown that in conditions of apparent physiological pacing as judged from right-sided AV intervals within a physiological range, non-physiological left heart AV intervals may result. Furthermore, it is well known that non-physiological left heart AV intervals may produce impairment of ventricular function. Thus, depending on whether the right atrium and right ventricle are paced or sensed, there will be alteration or not on the left heart AV interval. When the right atrium is sensed, there is no change in the left heart AV when the right ventricle is sensed as well, but the LAV will lengthen when the right ventricle is paced. When the right atrium is paced, there is a shortening in LAV when the right ventricle is sensed, but if the right ventricle is also paced, the delays may partially cancel out.

OBJECTS

It is accordingly a principal object of the invention is to provide a new and improved method and apparatus for automatically adjusting right heart AV interval to optimize left heart AV interval by compensating for pacing-induced inter-atrial and inter-ventricular delays.

It is a further object of the present invention to provide a dual-chamber AV sequential pacemaker that will compensate for the left heart AV interval.

It is another object of the invention to provide a new and improved method and apparatus for calculating left heart AV interval during cardiac pacing from right ventricular chambers.

SUMMARY OF THE INVENTION

The foregoing objects and advantages of the invention are achieved by providing an algorithm for a dual chamber AV sequential pacemaker providing the capability to compensate for pacing-induced inter-atrial and inter-ventricular conduction delays. This results in a pacer in which the right heart AV interval is automatically adjusted so as to optimize the left heart AV interval.

Conventional DDD and DDDR circuitry are utilized, and programming of sensor rate control is optional. The patient's intrinsic lower rate and AV interval determine the pacing and sensing actions required. According to these requirements, the pacemaker selects an appropriate AV interval. Values for inter-atrial and inter-ventricular delays are either assumed or measured via standard non-invasive techniques and programmed into the pacemaker. In this manner, a right AV interval that will compensate for these delays is automatically chosen by the pacemaker.

DESCRIPTION OF THE PREFERRED EMBODIMENT

Figure 1:
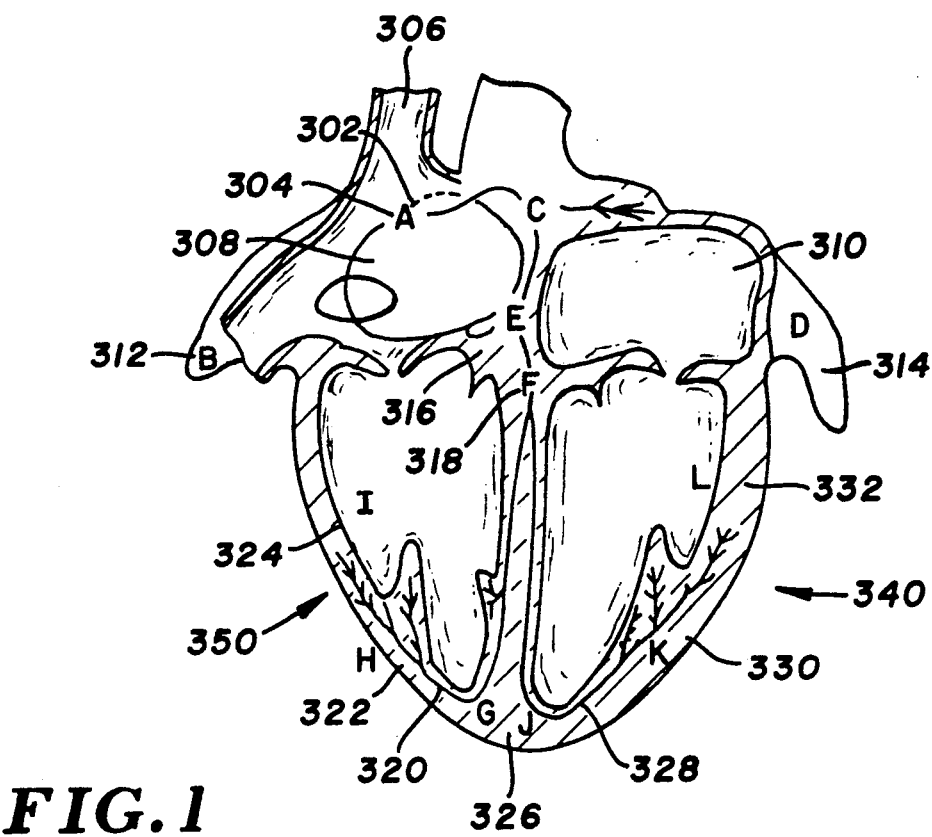
FIG. 1 depicts the anatomy of the conduction tissues of the heart.
Figure 2:
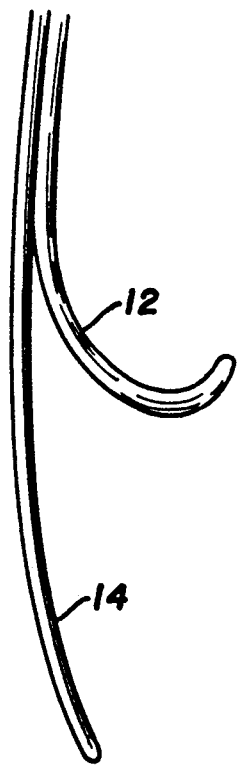
FIG. 2 shows a typical lead configuration used in the system.
Figure 3C:
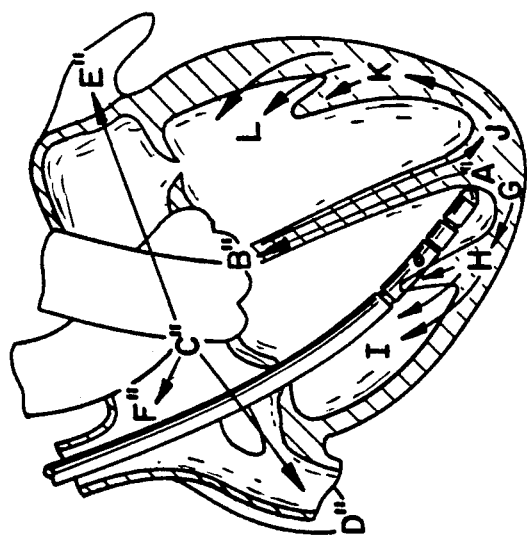
FIG. 3 shows the cardiac depolarization pathways in the normal heart (a), during right atrial pacing (b) and during right ventricular pacing (c).
Figure 3B:
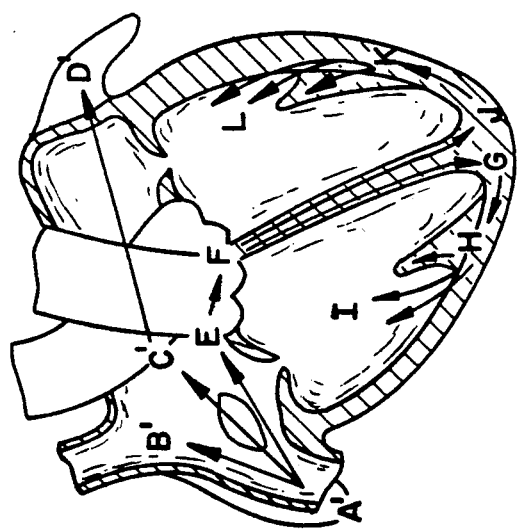
Figure 3A:
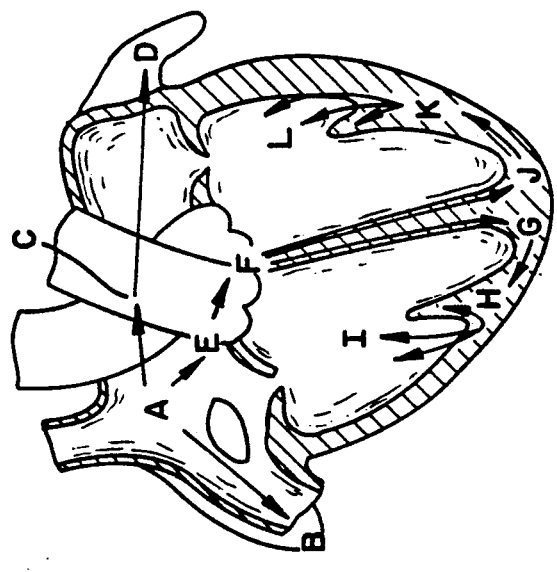
Figure 4:
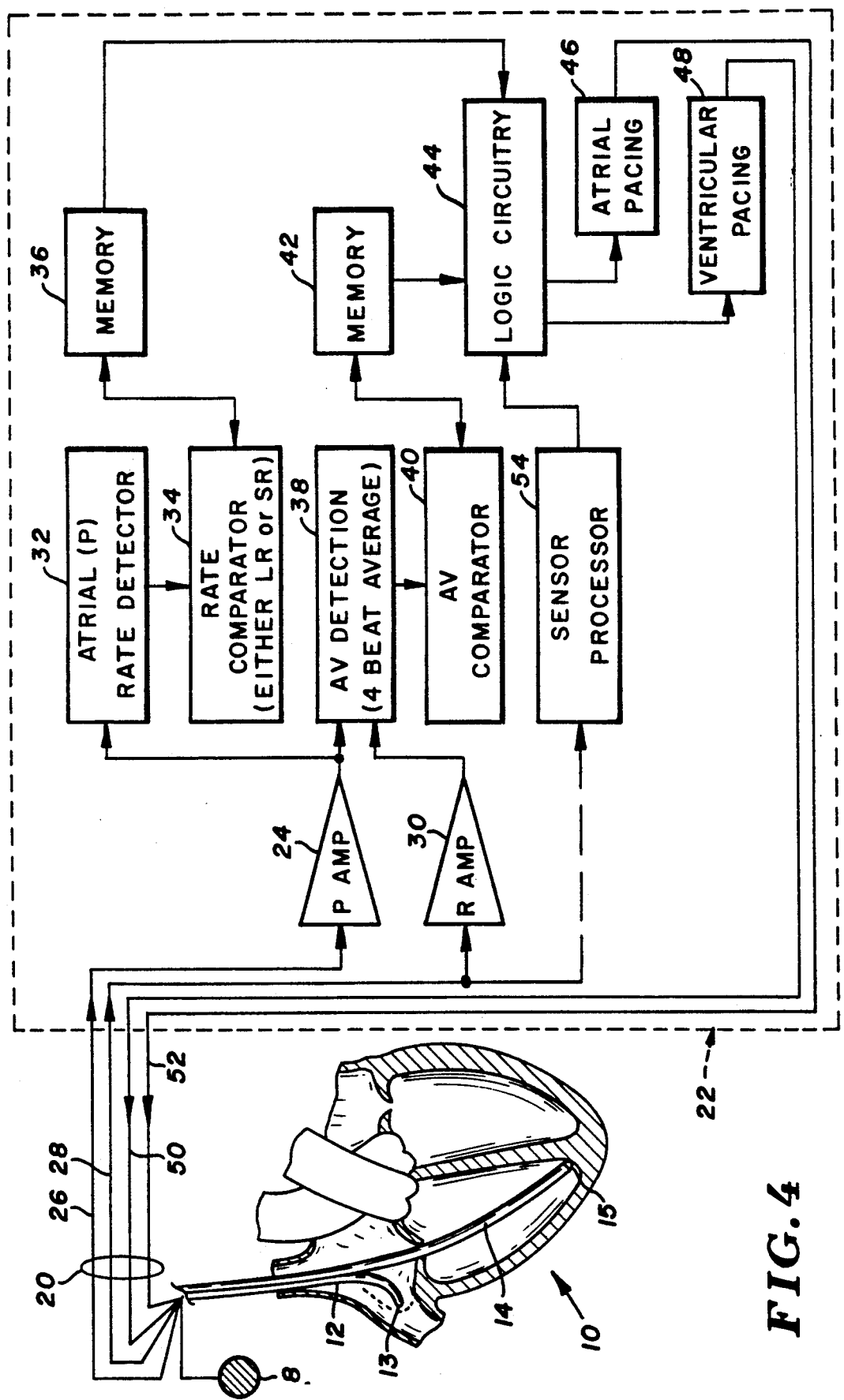
FIG. 4 is a functional block diagram of an apparatus that embodies the teachings of the present invention.

A preferred embodiment of the cardiac stimulating apparatus incorporating the present invention is shown in the block diagram of FIG. 4. In this drawing there is depicted schematically a heart 10 having 2 distinct leads, one in the artrium 12 and another in the ventricle 14. The lead 12 is shown as being passed through the superior vena cava and through the right atrium with tip electrode 13 projecting into the right atrial appendage and the lead 14 is shown with tip electrode 15 positioned at the apex of the right ventricle.

it comprises conventional DDD circuitry with rate control by a sensor (DDDR). Depending on the pacing and sensing action, as determined by the patient's own rate, sensor rate and intrinsic atrio-entricular (AV) interval, the pacemaker selects an appropriate pacing AV interval. Right heart AV is accommodated to compensate for inter-atrial and inter- entricular delays. These values can be calculated using non-invasive techniques and programmed into the pacemaker or alternatively default values may be used. Default inter-atrial conduction time (IACT) and interventricular conduction time (IVCT) typically may consist of average values observed in the paced population.

The pacing algorithm of the present invention described hereinbelow demonstrates one of the many ways by which compensation of left heart AV interval may be accomplished, and is based on the following premises:

1. Pacing the right atrial appendage causes a delay in left atrial contraction (inter-atrial conduction time, IACT).

2. Pacing the right ventricular apex causes a delay in left ventricular contraction, similar to that observed in Left Bundle Branch Block.

3. Atrial contribution to ventricular systole is dependent on AV interval.

4. Maintenance of left heart AV sequence is more important than right heart AV sequence for preservation of left ventricular efficiency.

The pacemaker has a 2 stage operating mechanism:

1. An Analysis Stage, during which it analyzes the timing of a programmable number of beats, for example 4 consecutive beats of the patient's intrinsic rhythm, and measures 4 AV intervals, obtaining a moving average refreshed every beat. AV interval during this stage is set at 250 ms to allow ample range for intrinsic AV intervals.

2. A Pacing Stage, during which a programmable number of beats are paced, for example the next 100 consecutive beats, according to the measured values (intrinsic AV, P wave rate), the other selected operating parameters of the pacemaker (left heart AV, lower rate, upper rate and other conventional variables) and sensor rate. The pacing AV interval will be selected so as to provide a left AV interval within a physiological range.

With particular reference to FIG. 4, there is depicted schematically a heart 10 having a multi-lead pacing/sensing apparatus disposed therein. The lead 12 is shown having electrode 13 for pacing the right atrium and the lead 14 having electrode 15 positioned at the right ventricular apex. A proximal indifferent electrode 18 is located outside of the heart.

Passing through the body of lead 12 there are 1 or 2 conductors (unipolar or bipolar configuration) plus the necessary conductors and/or hardware for sensor control of heart rate, to be connected in the usual manner to the implantable stimulator device enclosed by dashed line box 22.

The rate detection and stimulating apparatus enclosed by the dashed line box 22 includes a sense amplifier unit 24 having its input connected by a conductor 26 to the tip electrode 13 of the lead 12. The sense amplifier unit 24 is thus able to detect and amplify signals from the P wave segment of the standard electrocardiogram resulting from the beating action of the heart 10. An additional sense amplifier 30 detects and amplifies the QRS complex of the standard electrocardiogram in a similar manner. The output from the sense amplifier unit 24 is fed to a rate detector circuit 32 which, as its name implies, converts the detected P—P interval to a rate value, $R_1$, measured in beats/minute. This measured heart rate value, $R_1$, is then compared to a predetermined rate reference value, $R_2$, as indicated by block 34 and stored in memory 36. This value is used to determine pacing mode.

To evaluate the AV interval, the stimulator module 22 further includes an R wave sensor and amplifier 30 and AV detect circuitry 38 for detecting the right AV interval of the heart. AV interval is measured as the time elapsed between atrial and ventricular depolarizations, reflected as the time difference between either the native P wave or an atrial pacing spike and the native R wave or a ventricular pacing spike.

A programmable number of AV intervals will be evaluated by AV detector 38. A suggested number of intervals that will give a reliable average is 4. The detected value signal for AV interval from detector 38 is passed to AV comparator 40. When programmed to compute the average of 4 consecutive native AV intervals, this 4 beat average is compared to a predetermined, fixed threshold of, for example, 170 msec. The result of this comparison is stored in memory 42 and used by logic circuitry 44 to select and execute pacing mode. Either atrial pacing 46 or ventricular pacing 48 or both may be chosen. Stimulating pulses are then delivered via conductors 50 and 52. Thus, pacing and sensing of the right atrium may share the same atrial lead electrodes, and pacing and sensing of the ventricle may share the same ventricular lead electrodes.

The pacemaker incorporating the novel timing mechanism of the present invention utilizes standard sensing methods. Among these are various alternatives for sensor-controlled rate responsive pacing. Sensor signals may be obtained from ventricular leads or leads external to the heart. Examples of standard control parameters that may be derived from ventricular leads are stroke volume (volume of blood expelled from the ventricle during a single beat), first derivative of volume with respect to time, pressure, temperature, respiratory interval, electrocardiogram or Q-T interval. An example of an external control parameter is the signal derived from a motion sensor. Any one of these signals can be received in the manner known in the art by sensor processor 54, which contains standard circuitry for the execution of sensor controlled rate responsive pacing. In this example of the preferred embodiment, the sensor used is of the impedance detection type, whereby a driving signal is directed to the intraventricular electrodes, and the resulting voltage is detected from the same electrodes and processed in sensor processor 54 and then directed to logic circuitry 44 to determine the pacing rate. Thus either a programmed lower rate or a sensor-determined rate may control pacing rate in this device.

ANALYSIS STAGE

Figure 5:
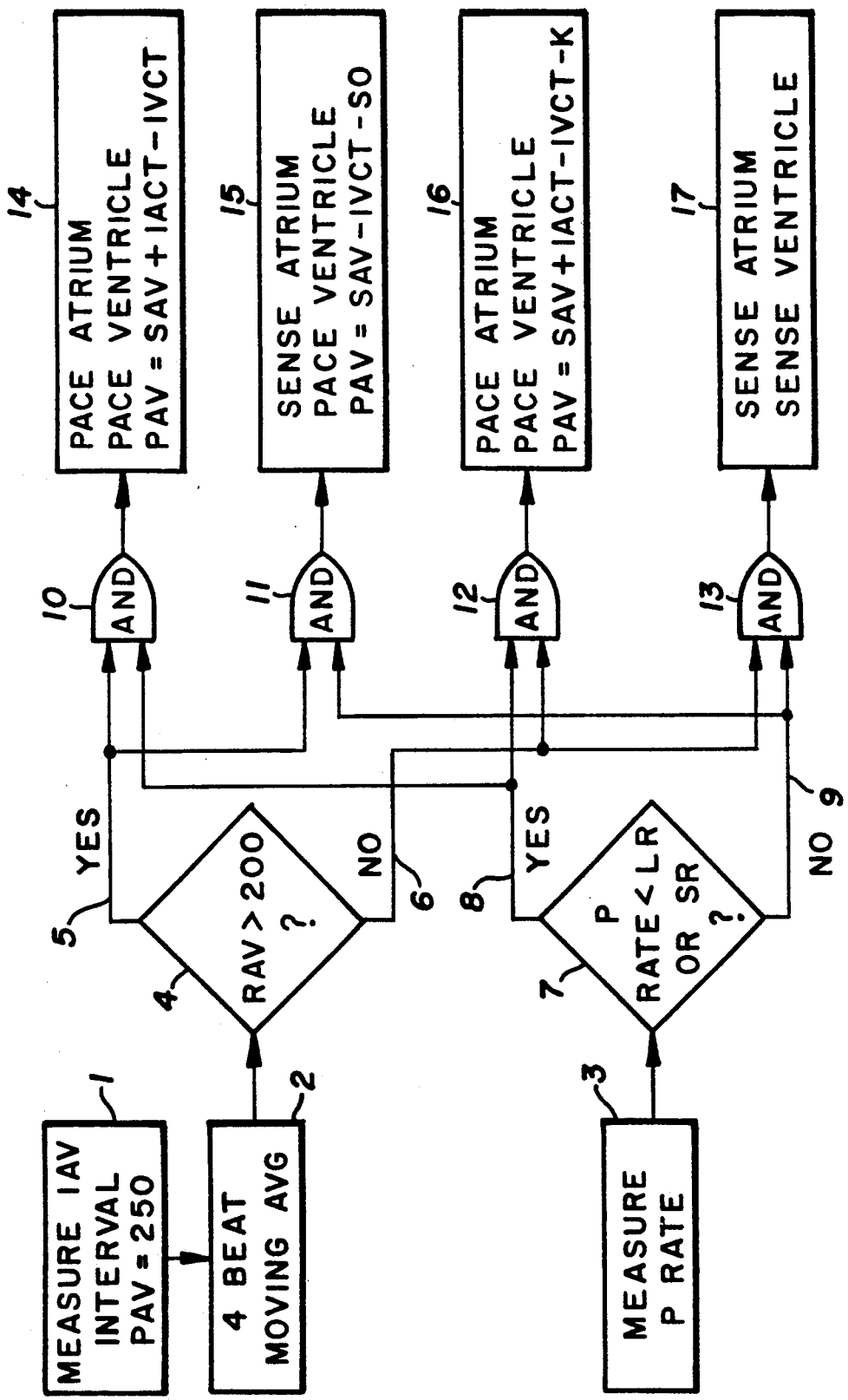
FIG. 5 depicts a software flow diagram of the preferred algorithm allowing for compensation of left heart AV interval in accordance with the present invention.

With reference to FIG. 5, the pacemaker first sets a long AV interval (i.e. 250 ms), to permit the measurement of 4 consecutive intrinsic AV intervals (IAV) (block 1) and obtain a moving average of them (block 2). Simultaneously, and on a beat-by-beat basis, the pacemaker measures the P wave rate (block 3).

As shown by decision block 4, a comparator directs a logic state 1 to "yes" output (5) if the measured average AV is greater than a reference value of, for example, 200 ms. A logic state 1 is directed to "no" output (6) if the patient's intrinsic AV is equal to or less than the reference value of 200 ms.

Similarly, and on a beat by beat basis, the patient's P wave rate is compared at decision block 7 with the pacemaker's lower rate (LR) (in DDD devices) or with the prevailing sensor rate (SR) (in DDDR devices). If the intrinsic rate is lower than either the LR or SR, a logic state 1 is directed to "yes" output (8). If equal or greater than the reference values, then the logic state 1 is directed to "no" output (9).

The outputs of comparators 4 and 7 directed to logic AND gates 10 through 13 to execute pacing mode. It can be seen that any combination of sensing or pacing the ventricle while sensing or pacing the atrium is possible, as indicated by blocks 14 through 17.

PACING STAGE

The pacemaker has registers for storing conventional programmable parameters, such as upper rate, lower rate, sensitivity, refractory periods, etc., and in addition, the values for inter-atrial and inter-ventricular conduction delays and selected left heart AV interval (SAV). Optionally, a P wave sensing offset (PSO) may be included. PSO is the difference resulting between AV intervals of paced atrial beats and sensed atrial beats. Since sensing of P waves take some time, this time slightly lengthens the AV interval.

Depending on the results of the comparisons at decision blocks and 7, logic AND gates 10 through 13 and values of IACT and IVCT, the pacing modality and AV interval are selected.

Assuming, for example, that IACT is 120 ms, IVCT is 60 ms and P Sensing Offset is 40 ms, the pacing AV interval will depend on whether the atrium and ventricle are sensed or paced. For example, if the selected left heart AV interval (SAV) is 150 ms, the patient's intrinsic AV is greater than 200 ms, and intrinsic rate is below the lower rate or sensor rate, AND gate 10 will be activated and the pacemaker will sequentially pace the atrium and ventricle with an AV interval of:

$$AV = SAV + IACT - IVCT = 150 + 120 - 60 = 210$$
ms (block 14).

In this case, it can be seen that in order to obtain a left heart AV of 150 ms, the right heart should be paced with an AV of 210 ms.

Likewise, if in the same patient the intrinsic P wave rate goes up, then comparator 7 will have a "no" output (line 9), and comparator 4 will continue with a "yes" output (Required condition: IAV > 200 ms). In this case, AND gate 11 will be active, and the pacemaker will track the P waves, pacing the right ventricle with an AV delay of:

$$AV = SAV - IVCT - SO = 150 - 60 - 40 = 50 \text{ ms},$$

to provide the left heart with an AV of 150 ms (step 15), which is physiological, and exactly as programmed.

In contrast, if the sensor rate prevails, thus driving the atrial channel, and if intrinsic AV is shorter than reference value (in this case 200 ms as compared to 180 ms), then pacing the atrium alone in this patient, as it would be the case with a conventional DDDR device, would cause the left heart AV to be:

$$LAV = IAV - IACT = 180 - 120 = 60 \text{ ms},$$

This is too short, thus it falls within a non-physiological range. The only way to delay left ventricular contraction in this situation is to accomplish a more physiological left heart AV interval by pacing the apex of the RV, which will introduce a delay in left ventricular activation equal to the inter-ventricular conduction delay. The Pacing AV would thus be:

$$PAV = SAV + IACT - IVCT - K = 150 + 120 - 60 - 40 = 170 \text{ ms}.$$

In this case, with a pacing AV of 170 ms, the effective left AV will be:

$$LAV = PAV - IACT + IVCT = 170 - 120 + 60 = 110$$
ms.

A constant, K, of 40 ms is used to offset the R wave sensing delay and to reduce the occurrence of fusion phenomenon. Fusion beats are those which occur when the pacing spike and the QRS complexes are superimposed upon the other.

Lastly, if the intrinsic rate is faster than the sensor rate, (decision block 7 with "no" output) and intrinsic AV is less than 200 ms (decision block 4 with "no" output), both chambers will be sensed by the pacemaker (step 17), in which case right and left AV intervals will be similar at 180 ms, the patient's own AV delay.

It is known from experiments on many patients that each patient has an optimal AV interval. In particular, the formula LAV = AV − IACT + IVCT expresses the relationship wherein left AV interval is equal to the difference between measured AV interval and inter-atrial conduction time plus interventricular conduction time. From this formula, and the examples given in the discussion of the prior art, it can be seen that programming a pacemaker to preserve an AV interval that falls within physiological range may not give accurate timing on the left heart when based upon measurements of right-sided events. This occurs because of the pathway of the depolarization and the fact that the timing of the left atrial and left ventricular depolarizations are difficult to assess from a standard surface ECG.

As is known in the art, both the sensing and pacing modes can be programmable. This particular 4/100 cycle sequence or any similar ratio, permits rapid corrections of pacing mode as cardiac conditions change. An example of such change would be intermittent heart block due to exercise. Therefore, the device permits enhanced flexibility to rapidly respond to such changes. Those values however are modifiable, tailoring them to the individual patient's needs. It can be seen then that when the DDD pacer is operated in accordance with the algorithm illustrated in FIG. 5, the right heart AV interval can be automatically adjusted so as to optimize the left heart AV interval. This is accomplished by compensating for pacing-induced inter-atrial and inter-ventricular conduction delays that naturally result from placement of the pacing stimulus at a site that is distant from the sinoatrial node. This is also accomplished by selecting threshold delay intervals that compensate for the different requirements depending upon whether the atrium is being paced or whether naturally occurring P waves are present.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. In a cardiac pacemaker of the type including a means for sensing atrial depolarization signals, means for sensing ventricular depolarization signals, control means for receiving said atrial and ventricular depolarization signals, atrial and ventricular pacing means for applying stimulating pulses to the atrium and to the ventricle, said pacemaker further including an improved timing means in said control means comprising:
   (a) means coupled to said atrial sensing means for determining whether the rate at which said atrial depolarization signals occur are below a first predetermined value;
   (b) AV interval determining mean coupled to said atrial and said ventricular sensing means for determining whether the time between the occurrence of an atrial depolarization signal and the next succeeding ventricular depolarization signal, on the average, exceeds a predetermined AV interval value and if so, triggering said ventricle pacing means to generate a series of ventricular stimulating pulses, each ventricular pulse following a predetermined time delay from the preceding atrial depolarization signal; and
   (c) means for adjusting pacing induced AV interval and for producing an effective left heart AV interval corrected for pacing-induced timing delays which result from whether the artrium and/or ventricles are being paced or sensed.

2. The device as in claim 1, wherein said atrial sensing means further comprises means for detecting the presence or absence of a native atrial beat and if no native atrial beat is detected within a pre-established physiologic time interval, sense a control signal to said atrial pace means to apply said stimulating pulse to the atrium before engaging said AV interval determining means.

3. The device as in claim 1, wherein said AV interval determining means further includes means for evaluating a predetermined number of AV intervals and determining the average thereof, and comparator means for comparing said average AV interval to said predetermined AV interval value.

4. The device as in claim 1 further comprising means for receiving external programming data wherein said predetermined AV interval value is programmable.

5. The device as in claim 1, wherein said means coupled to said atrial sensing means for determining atrial depolarization rate further includes an atrial rate detection means for detecting the time interval between a first and a second native atrial depolarization and an atrial rae comparator means for determining if the rate at which sad second naive atrial depolarization occurs is below a second predetermined value.

6. The device as in claim 1, wherein said atrial sensing means further includes comparator means for comparing native atrial rate to a discrete predetermined lower rate value and logic means coupled to said comparator means for activating said atrial pacing mean sand said ventricular pacing means depending on the results of the comparison.

7. The device as in claim 3, and further including comparator means coupled to said atrial sensing means for comparing measured atrial rate with a predetermined reference value and controlling said atrial and ventricular pacing means.

8. The device as in claim 3, further comprising means for determining a right heart AV interval to optimize said produced left heart AV interval.

9. The device as in claim 3, wherein the adjusting means produces the effective left heart AV interval as a function of a predetermined lower rate or sensor rate provided by a sensor coupled thereto and whether either the atrium or ventricle or both are paced or sensed.

* * * * *

UNITED STATES PATENT AND TRADEMARK OFFICE
CERTIFICATE OF CORRECTION

PATENT NO. : 5,179,949
DATED : January 19, 1993
INVENTOR(S) : Raul Chirife

It is certified that error appears in the above-identified patent and that said Letters Patent is hereby corrected as shown below:

Column 10, line 32, delete "rae" and put instead -- rate --.

Column 10, line 33, delete "sad" and put instead -- said --.

Column 10, line 39, delete "mean sand" and put instead -- means and --.

Signed and Sealed this

Twenty-third Day of November, 1993

Attest:

BRUCE LEHMAN

Attesting Officer

Commissioner of Patents and Trademarks